US008485968B2

(12) United States Patent
Weimer et al.

(10) Patent No.: US 8,485,968 B2
(45) Date of Patent: Jul. 16, 2013

(54) ENDOSCOPE

(75) Inventors: Eugen Weimer, Essingen (DE); Hubert Czujack, Geisingen (DE)

(73) Assignee: Sopro-Comeg GmbH, Tuttlingen (DE)

( * ) Notice: Subject to any disclaimer, the term of this patent is extended or adjusted under 35 U.S.C. 154(b) by 0 days.

(21) Appl. No.: 13/368,422

(22) Filed: Feb. 8, 2012

(65) Prior Publication Data
US 2012/0136213 A1 May 31, 2012

Related U.S. Application Data

(63) Continuation of application No. PCT/DE2010/001189, filed on Oct. 11, 2010.

(30) Foreign Application Priority Data

Oct. 12, 2009 (DE) .................... 10 2009 049 143

(51) Int. Cl.
*A61B 1/06* (2006.01)
(52) U.S. Cl.
USPC ............ 600/173; 600/163; 600/167; 600/174
(58) Field of Classification Search
USPC ...................... 600/170–171, 173–176, 140
See application file for complete search history.

(56) References Cited

U.S. PATENT DOCUMENTS

| 3,856,000 | A | * | 12/1974 | Chikama ...................... 600/173 |
| 4,697,577 | A | * | 10/1987 | Forkner ........................ 600/173 |
| 5,359,992 | A | * | 11/1994 | Hori et al. ........................ 126/4 |
| 6,537,210 | B1 | | 3/2003 | Wulfsberg |
| 6,616,602 | B1 | * | 9/2003 | Witte .............................. 600/167 |
| 6,916,286 | B2 | * | 7/2005 | Kazakevich ................... 600/173 |
| 6,919,914 | B2 | * | 7/2005 | Beutter et al. .................. 348/65 |
| 2002/0049366 | A1 | | 4/2002 | Kehr |
| 2004/0015049 | A1 | | 1/2004 | Zaar |
| 2004/0236183 | A1 | | 11/2004 | Durell |
| 2010/0030031 | A1 | | 2/2010 | Goldfarb et al. |

FOREIGN PATENT DOCUMENTS

| DE | 19903437 C1 | 8/2000 |
| DE | 19927816 A1 | 1/2001 |
| JP | 2008272445 A | 11/2008 |

OTHER PUBLICATIONS

European Patent Office, International Search Report in International Patent Application No. PCT/DE2010/001189 (Aug. 3, 2011).

* cited by examiner

*Primary Examiner* — Alireza Nia
(74) *Attorney, Agent, or Firm* — Leydig, Voit & Mayer, Ltd.

(57) ABSTRACT

A rigid, rod-shaped endoscope for medical applications includes a distal end having a light-permeable distal window and a light outlet disposed adjacent to the distal window, which includes a device configured to prevent the incidence of stray light onto sides of the deflection prism facing the distal window. An endoscope shank includes a plurality of telescoping hollow tubes. An inner fixed optical tube includes a moveable optical deflection prism and an optical system configured to transmit light beams. The optical deflection prism is mounted rotatably on a shaft that is disposed at a right angle to a longitudinal axis of the endoscope. At least one moveable sliding tube is configured to move relative to the inner fixed optical tube in the direction of the longitudinal axis of the endoscope using magnetic forces generated by a plurality of moveable permanent magnets.

9 Claims, 6 Drawing Sheets

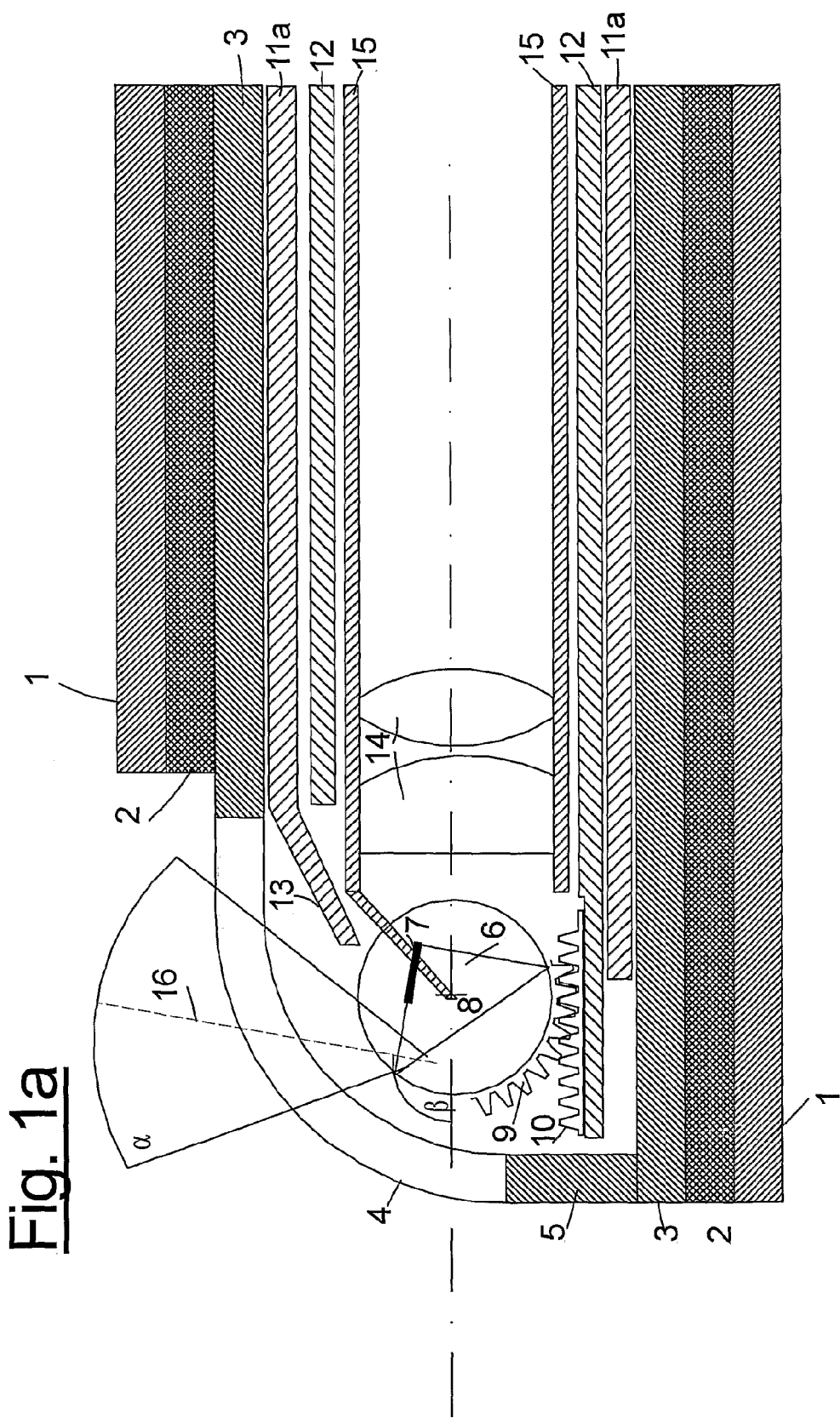

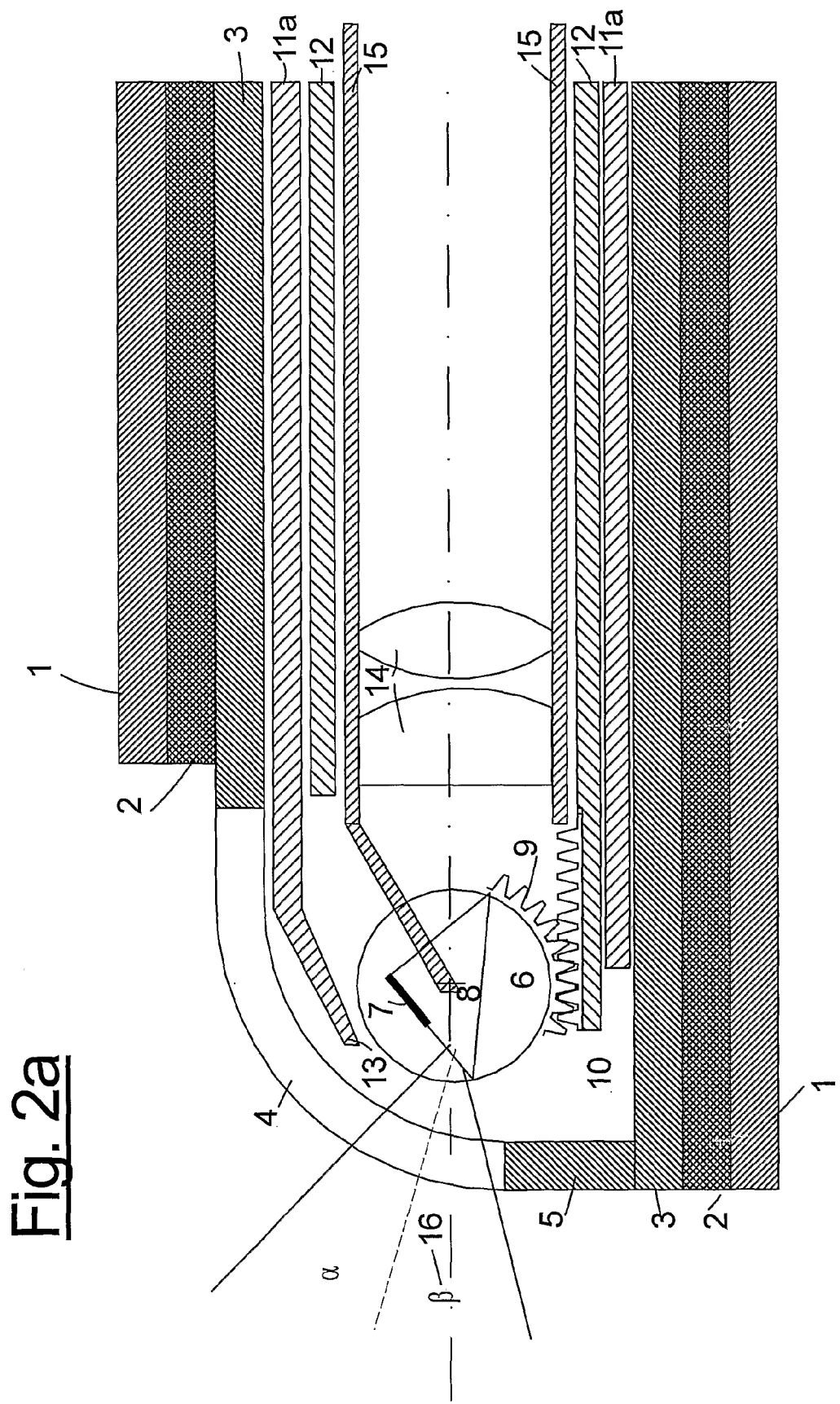

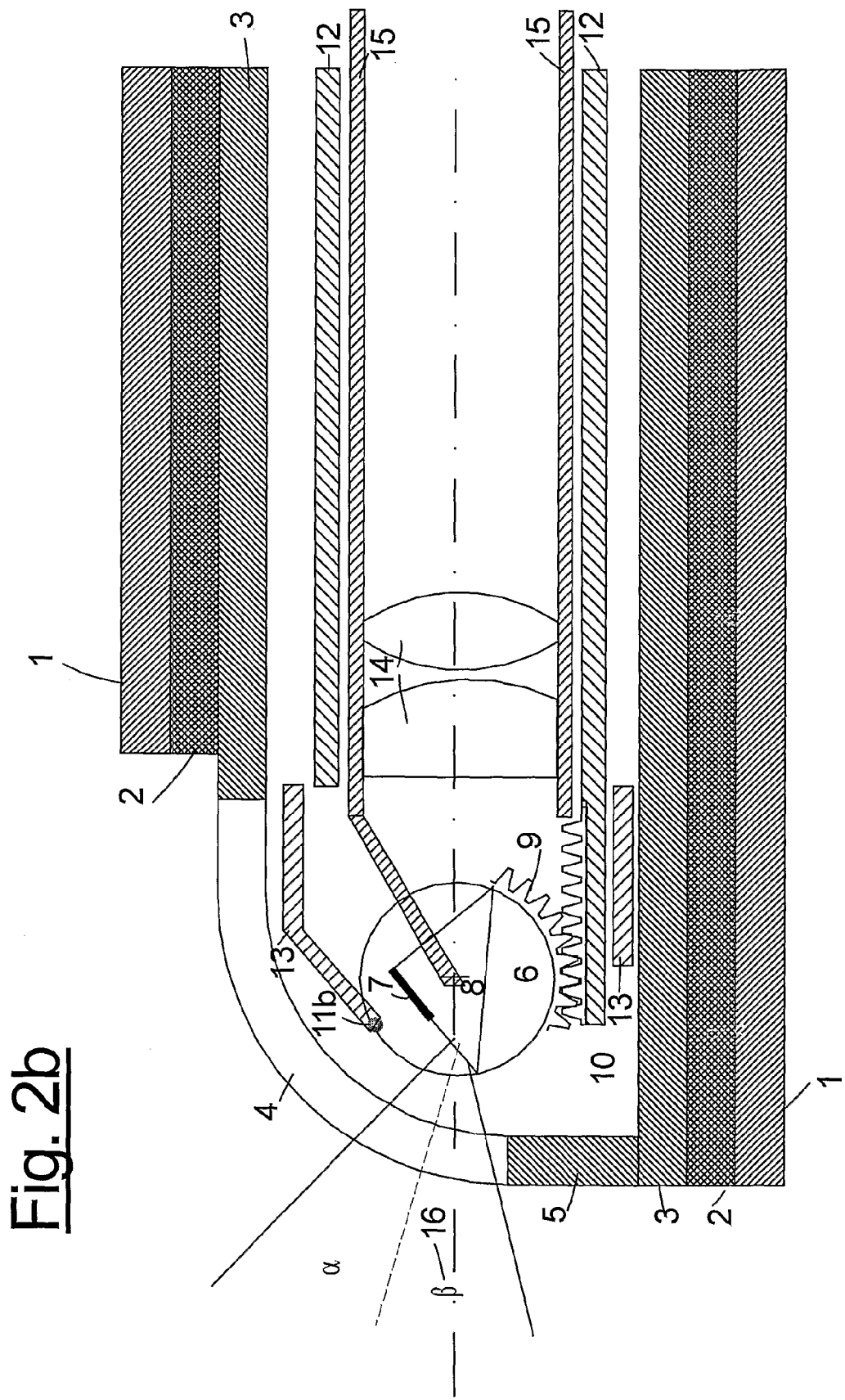

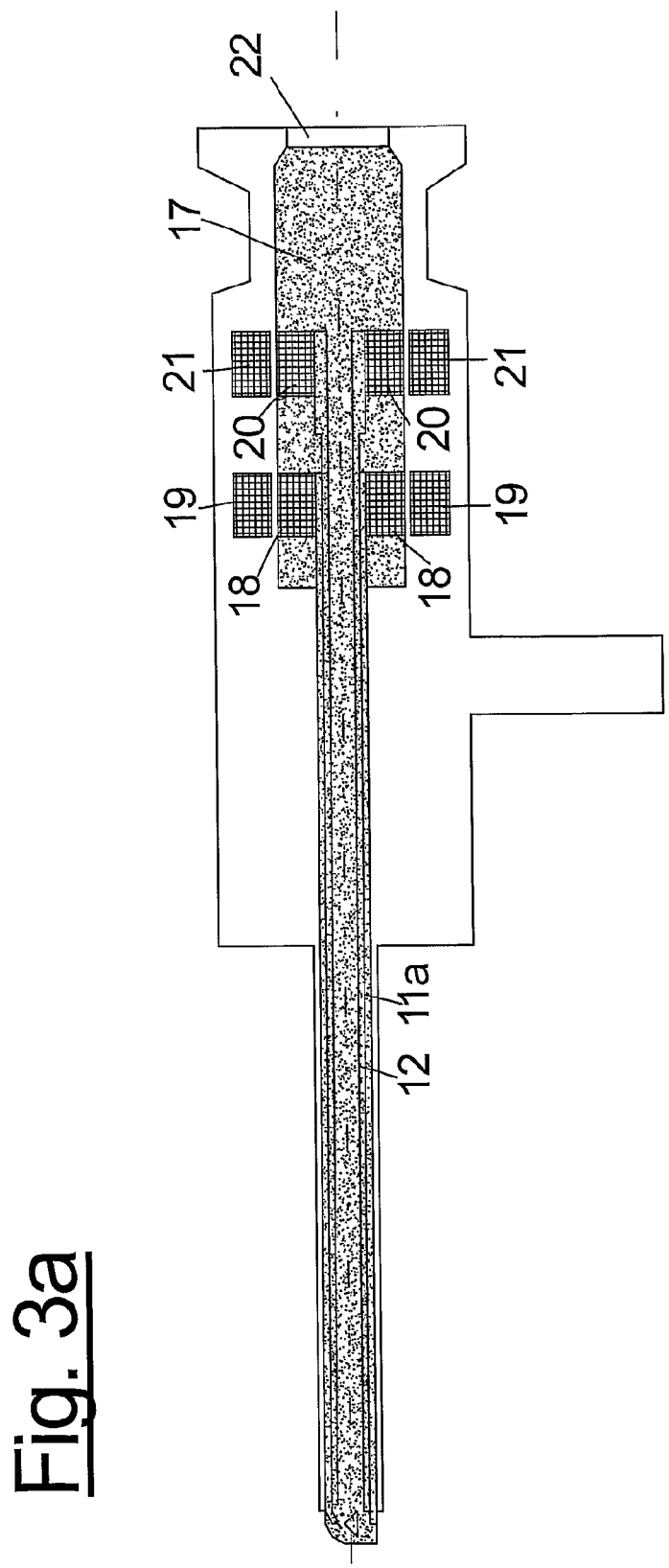

ENDOSCOPE

CROSS-REFERENCE TO PRIOR APPLICATION

This application is a continuation of International Patent Application No. PCT/DE2010/001189, filed on Oct. 11, 2010, which claims priority to German Patent Application No. DE 10 2009 049 143.0, filed on Oct. 12, 2009. The entire disclosure of both applications is hereby incorporated by reference herein.

FIELD

The invention relates to a rigid endoscope for medical applications that is suitable for autoclave sterilization and in which various viewing directions can be set.

BACKGROUND

Medical endoscopes normally serve to examine internal organs in a body cavity. For this purpose, either a natural body opening is used or else an incision is made in the body through which the endoscope is inserted all the way to the point of observation. At the distal end of the endoscope, there is a light source for illumination purposes and a window through which the light reflected from the object can enter the endoscope, after which the light is conveyed through an optical device to the proximal end of the endoscope to the observer or to an image-capturing device.

After the endoscope has been used, it has to be cleaned, disinfected and sterilized in order to avoid spreading infection between patients. The sterilization is quite problematic. There is a need to use either toxic substances which subsequently have to be removed with a great deal of effort, or else steam, which can cause problems in terms of achieving a tight seal.

In order to prevent the procedure from causing discomfort to the patient, there is a desire to use the endoscopes that are as thin as possible. This means that the optical devices have to meet high requirements. Moreover, it should be feasible to perform as many examinations as possible with the same endoscope, since every time the endoscope is replaced, this involves physical discomfort for the patient.

An endoscope with a magnetic adjustment device is described in German patent application DE 199 27 816 A1. The endoscope includes a sealed housing wall and a structural element that is arranged on the inside and that can be adjusted by means of a drive element that is attached to the structural element and that can be moved by a magnetic field through the wall by means of a magnet situated outside of the wall. However, the movement is brought about by an external magnet that is structurally separated from the endoscope.

An endoscope is described in U.S. Pat. No. 3,856,000 having an arrangement wherein the light incidence through the front entrance surface of the prism is not limited and the prism is tilted by means of a wire pull that takes up a great deal of space.

SUMMARY

In an embodiment, the present invention provides a rigid, rod-shaped endoscope for medical applications. A distal end includes a light-permeable distal window and a light outlet disposed adjacent to the distal window. The distal window includes a device configured to prevent the incidence of stray light onto sides of the deflection prism facing the distal window. An endoscope shank includes a plurality of telescoping hollow tubes, two of the hollow tubes forming an outer jacket tube with the distal window. An inner fixed optical tube includes a moveable optical deflection prism disposed so as to face the distal window and an optical system disposed inside the inner fixed optical tube and configured to transmit light beams. The optical deflection prism is mounted rotatably on a shaft that is disposed at a right angle to a longitudinal axis of the endoscope. The inner fixed optical tube is disposed in a tightly and hermetically sealed chamber formed by the outer jacket tube so as to allow an outside of the outer jacket tube to be sterilized by steam. At least one moveable sliding tube is disposed between the outer jacket tube and the inner fixed optical tube and is configured to move relative to the inner fixed optical tube in the direction of the longitudinal axis of the endoscope using magnetic forces generated by a plurality of moveable permanent magnets. At least one of the permanent magnets is disposed inside the hermetically sealed chamber and at least one of the permanent magnets is disposed outside of the hermetically sealed chamber. The sliding tube is connected to the optical deflection prism at the distal end such that movement of the sliding tube in the direction of the longitudinal axis of the endoscope causes the optical rotation prism to rotate around the shaft. A proximal end includes at least one of an optical observation device and a camera adapter.

BRIEF DESCRIPTION OF THE DRAWINGS

The present invention will be described in even greater detail below based on the exemplary figures. The invention is not limited to the exemplary embodiments. Other features and advantages of various embodiments of the present invention will become apparent by reading the following detailed description with reference to the attached drawings which illustrate the following.

DETAILED DESCRIPTION

Figure 1B:
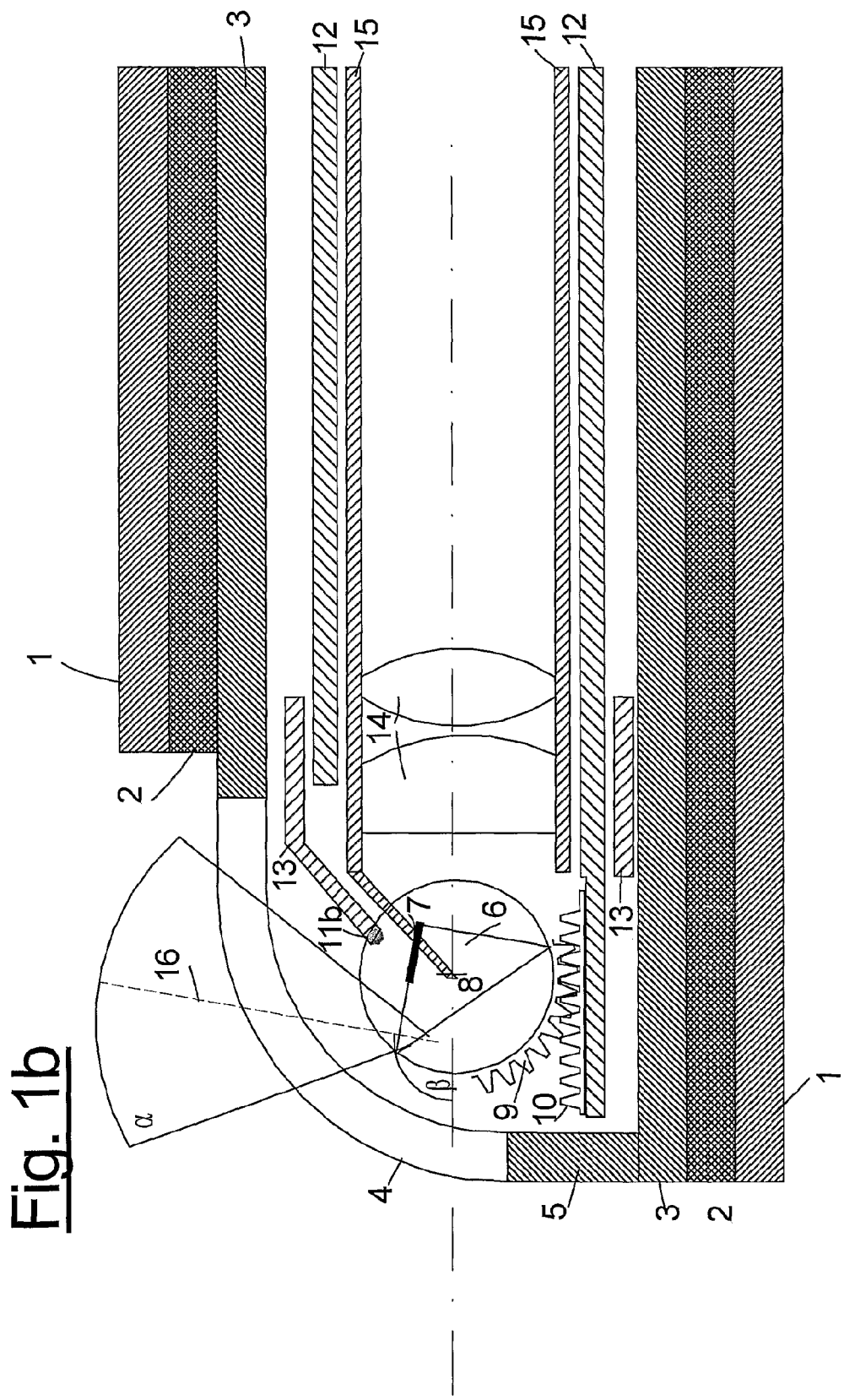
FIGS. 1a/b and FIGS. 2a/b show simplified schematic diagrams of a longitudinal section through the distal end of an endoscope according to an embodiment of the invention with the two end positions of a 90° prism shown by way of an example.

In an embodiment, the invention provides a rigid endoscope for medical applications that can easily be sterilized with steam, that allows many examinations without having to replace the endoscope, and that has the best possible optical quality while concurrently having a thin structure.

In an embodiment, the invention provides a rigid, rod-shaped endoscope for medical applications, having an outer jacket tube, an inner fixed optical tube and at least one moveable sliding tube located in-between, comprising a distal end with a light-permeable distal window and a light outlet located next to it, an optical deflection prism facing the distal window, 1a proximal end with an optical observation device or a camera adapter, an endoscope shank made up of telescoping hollow tubes, whereby the two outer hollow tubes form the jacket tube with a window at the distal end, the optical tube has the movable deflection prism at its distal window and, in its interior, it has an optical system for transmitting light beams, at least one sliding tube is arranged between the jacket tube and the optical tube, and this sliding tube can be slid in the direction of the longitudinal axis of the endoscope, on the distal window, there is device that can prevent the incidence of stray light onto the sides of the deflection prism facing the distal window, the deflection prism facing the distal window is mounted rotatably on a shaft that is at a right angle to the longitudinal axis of the endoscope, the sliding tube is connected at the distal end to the deflection prism in such a way that sliding this tube with respect to the optical tube leads to a rotation of the prism around its shaft, the jacket tube forms a tightly and hermetically sealed chamber that also completely surrounds the inner hollow tubes located therein, and whose tight seal makes it possible to sterilize the space around it with steam, the sliding tube is slid with respect to the optical tube by means of magnetic forces that are generated by movable permanent magnets, whereby at least one permanent magnet is arranged inside and at least one permanent magnet is arranged outside of the hermetically sealed chamber.

In an embodiment, the movements that are necessary inside the hermetically sealed chamber are transmitted exclusively by magnetic forces. As a result, a hermetically sealed chamber can be formed that no longer requires gaskets for sliding or rotating parts, and the possibility exists to carry out the sterilization with steam, so that the steam can no longer penetrate into the interior of the endoscope where the optical system is located, which, due to the play in the bearings, would otherwise have been inevitable because of the temperature changes and the expansions caused by the steam.

In an embodiment, the optical system can be configured in such a way that useful light only enters through the lower part of the side of the deflection prism facing the window. As a result, it is possible to use means to cover the rest of the prism in such a way that stray light is almost completely blocked off. In one embodiment of the invention, it is provided that the means with which the light incidence is limited on the side of the deflection prism facing the window is a blackening over approximately half of the surface of the deflection prism. Alternatively or additionally, it is provided that the means is an axially movable shutter. Such a shutter also protects the rear exit surface of the prism against the incidence of stray light striking at small deflection angles.

Thanks to such a device, stray light is kept away from the lens system of the endoscope. Here, because of the large observation space that an endoscope according to an embodiment of the invention permits, it can be ensured that such an endoscope also has a correspondingly powerful illumination device made up of optical fibers or diodes, so that this device can properly illuminate the observation space.

In view of this special feature, namely, illumination over a large surface and at a high intensity, the problem involving stray light is also correspondingly relevant. Another reason is that, in medical applications, the surfaces to be observed—unlike in technical applications—are usually very close to the endoscope and generate a high level of stray light intensity. As a result, the endoscope according to the invention differs from the state of the art that is described, for example, in U.S. Pat. No. 3,856,000, in which the light incidence through the front entrance surface of the prism is not limited and the prism is tilted by means of a wire pull that takes up a great deal of space.

These stray light influences are prevented by the blackening as well as by the shutter which has to shade all of the parts of the prism that face the window and that fall outside of the angle of view. As soon as the prism is tilted and the angle of view moves aside, the shutter has to be retracted. Consequently, the rotational movements of the prism and of the shutter are connected to each other. These coupled movements can be effectuated either by a joint sliding tube or by various hollow tubes or by a coupling of the movements with an articulation between the prism axis and the shutter. The use of a wire pull would take up too much space, especially in view of the small diameters of medical endoscopes.

In another embodiment of the invention, it is provided that the deflection prism is fitted with a toothed gear segment on the reflecting side, facing away from the distal window, and this segment engages with a toothed rack that is firmly connected to the sliding tube. The rotating shaft on which the deflection prism is installed is fastened to the optical tube that contains the optical devices for conveying the light beams. In this manner, a high precision can be ensured when the prism is adjusted, whereby at the same time, a very narrow design is achieved.

In another embodiment of the invention, it is provided that the magnetic forces are transmitted by at least one pair of permanent magnets, whereby one permanent magnet is affixed on the outside on the first inner hollow tube, while the other permanent magnet is mounted so as to slide on the outside of the second outer hollow tube. In another advantageous embodiment, it is provided that the permanent magnets are configured as annular magnets and are poled in such a way that they are pulled into the same cross sectional plane. In this manner, an especially favorable frictional connection is achieved.

In an embodiment of the invention provided by way of an example, it is provided that a 90° rectangular prism is used as the deflection prism and that a range from 10° to 110° can be set continuously as the angle of view relative to the longitudinal axis, and the field of view is about 60°. Whereas endoscopes according to the conventional state of the art only allow one single setting of the viewing direction and thus have to be replaced correspondingly often during the examination, the design according to an embodiment of the invention allows the examination to be made without replacing the instrument, which on the one hand, has the advantage of being easier on the patient and, on the other hand, has the advantage that fewer devices have to be sterilized after the examination, whereby the sterilization with steam can be carried out very quickly. All in all, this reduces the number of endoscopes that have to be kept on hand, which is a major financial advantage.

Referring to FIGS. 1a/b and 2a/b, the outer tube 1 protects the illumination system that, in this case, consists of an optical fiber bundle 2. Arranged therein is the second outer hollow tube 3 with the window 4 and the front part 5, which are tightly connected to each other. These elements form the jacket tube.

The rectangular prism 6 with the blackened area 7 is arranged in the hermetically sealed interior inside the jacket tube near the window. It is mounted rotatably on the shaft 8, the rotation is effectuated by means of the toothed gear segment 9, which is actuated by the toothed rack 10. Whereas the shaft 8 is affixed on the optical tube 15, which contains the optical system for conveying the light beams coming from the object under observation, the toothed rack 10 is moved by the sliding tube 12. Instead of a toothed gear segment with a toothed rack, it is also possible to use a different type of articulation that is capable of executing a rotating and tilting movement.

Figure 3B:
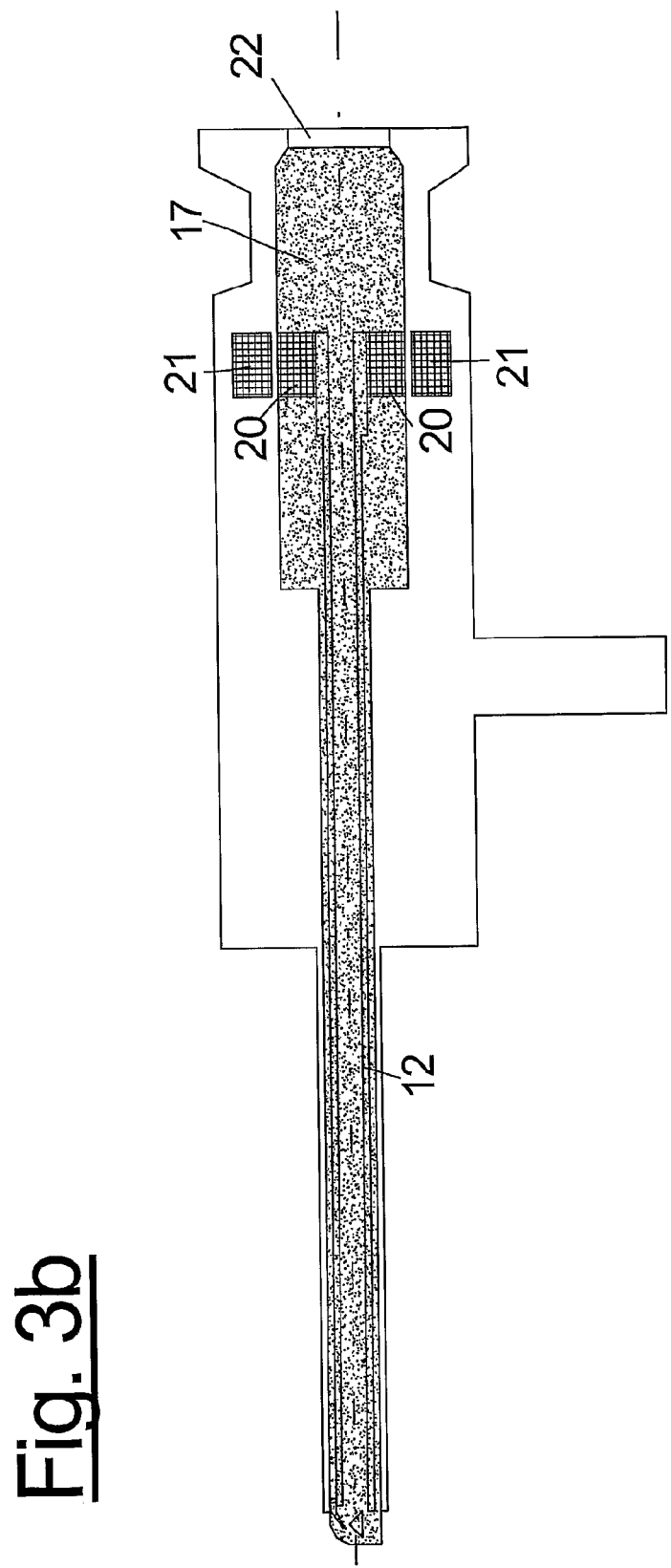
FIGS. 3a/b show schematic diagrams of the entire endoscope.

The depictions of FIGS. 1a, 2a and 3a differ from those of FIGS. 1b, 2b and 3b in terms of the movement of the shutter 13. FIGS. 1a, 2a and 3a show how the shutter 13 can be moved independently of the tilting of the deflection prism 6. For this purpose, aside from the sliding tube 12, another sliding tube is used, namely, the shutter sliding tube 11a, which is arranged outside of the sliding tube 12, but inside the jacket tube.

FIGS. 1b, 2b and 3b show how the shutter 13 can be moved in a coupled manner independently of the tilting of the deflection prism 6. Here, the shutter 13 is attached to the suspension device of the deflection prism 6 via an articulation 11b. When the shaft 8 rotates, the shutter 13 is pulled forward or retracted accordingly. An endoscope that is configured in this way can be designed so as to be simpler and thinner.

In FIGS. 1a and 1b, the angle of view α is 60°, and the mid-line of the field of view β is rotated by 100° relative to the horizontal. Therefore, the range between 130° and 70° relative to the horizontal can be viewed and examined. In FIGS. 2a/b, the angle of view is likewise 60°, and the mid-point of the field of view is rotated by 10° relative to the horizontal. Therefore, the range between 40° and −20° relative to the horizontal can be viewed and examined. This broad range makes high demands of the illumination system 2. Common structural configurations of embodiments of the invention achieve a tilting of the prism in such a manner that the field of view is up to 110° with a field of view of 60°±10°.

FIGS. 3a and 3b show schematic diagrams of the endoscope with a depiction of the hermetically sealed chamber 17, which is depicted filled with dots. The two depictions differ in terms of the movement of the shutter 13 and the corresponding arrangement and number of magnets.

In FIG. 3a, an annular magnet 18 is arranged inside the chamber 17; it is connected to the shutter sliding tube 11a, and it can be moved axially by means of an annular magnet 19 that is located above and outside of the chamber 17 and that can be slid axially. Moreover, another annular magnet 20 is located inside this chamber 17; said magnet is connected to the sliding tube 12, and it can be moved axially by means of an annular magnet 21 that is located above and outside of the chamber 17 and that can likewise be slid axially. The two outer annular magnets 19 and 21 are connected to each other in such a way that they move and can be adjusted in a defined relationship to each other, as a result of which the correct shutter setting is set at different angles of view.

In FIG. 3b, the magnets 18 and 19 can be dispensed with since the coupling of the movement of the shutter 13 is effectuated distally by the articulation 11b.

FIGS. 3a and 3b also show the arrangement of the hermetically sealed window 22 on the proximal end of the endoscope.

While the invention has been described with reference to particular embodiments thereof, it will be understood by those having ordinary skill the art that various changes may be made therein without departing from the scope and spirit of the invention. Further, the present invention is not limited to the embodiments described herein; reference should be had to the appended claims.

LIST OF REFERENCE NUMERALS 1 outer tube
2 optical fiber bundle
3 second outer hollow tube
4 window
5 front part
6 rectangular prism
7 blackened area
8 shaft
9 toothed gear segment
10 toothed rack
11a shutter sliding tube
11b articulation
12 sliding tube
13 shutter
14 optical system
15 optical tube
16 mid-line
17 chamber
18 annular magnet
19 annular magnet
20 annular magnet
21 annular magnet
22 window

What is claimed is:

1. A rigid, rod-shaped endoscope for medical applications, comprising:
   a distal end including a light-permeable distal window and a light outlet disposed adjacent to the distal window, the distal window including a device configured to prevent incidence of stray light onto sides of a moveable optical deflection prism facing the distal window;
   a proximal end including at least one of an optical observation device and a camera adapter;
   an endoscope shank including a plurality of telescoping hollow tubes, two of the hollow tubes forming an outer jacket tube with the distal window;
   an inner fixed optical tube including the optical deflection prism disposed so as to face the distal window and an optical system disposed inside the inner fixed optical tube and configured to transmit light beams, the optical deflection prism being mounted rotatably on a shaft that is disposed at a right angle to a longitudinal axis of the endoscope, the inner fixed optical tube being disposed in a tightly and hermetically sealed chamber formed by the outer jacket tube so as to allow an outside of the outer jacket tube to be sterilized by steam; and
   at least one hollow moveable sliding tube disposed between the outer jacket tube and the inner fixed optical tube, extending between the distal end and the proximal end, and configured to move relative to the inner fixed optical tube in the direction of the longitudinal axis of the endoscope using magnetic forces generated by a plurality of moveable permanent magnets disposed at the proximal end, at least one of the permanent magnets being disposed inside the hermetically sealed chamber and at least one of the permanent magnets being disposed outside of the hermetically sealed chamber, the sliding tube being connected to the optical deflection prism at the distal end such that movement of the sliding tube in the direction of the longitudinal axis of the endoscope by the permanent magnets at the proximal end causes the optical deflection prism to rotate around the shaft at the distal end.

2. The endoscope according to claim 1, wherein the device configured to prevent the incidence of stray light onto sides of the deflection prism facing the distal window includes a blackening over approximately half of the surface of the deflection prism.

3. The endoscope according to claim 1, wherein the device configured to prevent the incidence of stray light onto sides of the deflection prism facing the distal window includes an axially moveable shutter connected to the optical deflection prism such that a movement of the axially moveable shutter is directly coupled to a rotation, in a distal range, of the optical deflection prism.

4. The endoscope according to claim, wherein the device configured to prevent the incidence of stray light onto sides of the deflection prism facing the distal window includes an axially moveable shutter that is moveable by a shutter sliding tube configured to slide relative to the inner fixed optical tube in the direction of the longitudinal axis of the endoscope using magnetic forces generated by a plurality of moveable permanent magnets, at least one of the permanent magnets being disposed inside the hermetically sealed chamber and at least one of the permanent magnets being disposed outside of the hermetically sealed chamber.

5. The endoscope according to claim 3, wherein the axially movable shutter is moveable in the direction of the longitudinal axis of the endoscope by an articulation that has a movement that is coupled to the rotation of the optical deflection prism.

6. The endoscope according to claim 1, wherein the optical deflection prism includes a toothed gear segment on a side facing away from the distal window configured to engage with a toothed rack connected to the sliding tube, and wherein the shaft is connected to the inner fixed optical tube.

7. The endoscope according to claim 1, wherein the magnetic forces are generated by at least one pair of the permanent magnets, at least one of the pair of the permanent magnets being disposed on an outside of at least one of the at least one sliding tube and a shutter sliding tube and at least the other one of the pair of the permanent magnets being disposed so as to slide on the outside of the outer jacket tube in the direction of the longitudinal axis of the endoscope.

8. The endoscope according to claim 7, wherein the at least one pair of the permanent magnets are configured as annular magnets and include a polarity so as to be pulled into the same cross sectional plane.

9. The endoscope according to claim 1, wherein the endoscope includes a continuously settable angle of view of 10° to 110° relative to the longitudinal axis and a field of view is about 60°±10°.

\* \* \* \* \*